United States Patent
De Vries et al.

(10) Patent No.: US 9,199,961 B2
(45) Date of Patent: Dec. 1, 2015

(54) PREPARATION OF CAPROLACTONE, CAPROLACTAM, 2,5-TETRAHYDROFURAN-DIMETHANOL, 1,6-HEXANEDIOL OR 1,2,6-HEXANETRIOL FROM 5-HYDROXYMETHYL-2-FURFURALDEHYDE

(75) Inventors: Johannes Gerardus De Vries, Maastricht (NL); Teddy, Groningen (NL); Pim Huat Phua, Groningen (NL); Ignacio Vladimiro Melián Cabrera, Groningen (NL); Hero Jan Heeres, Harkstede (NL)

(73) Assignee: NEDERLANDSE ORGANISATIE VOOR WETENSCHAPPELIJK ONDERZOEK (NWO), The Hague (NL)

( * ) Notice: Subject to any disclaimer, the term of this patent is extended or adjusted under 35 U.S.C. 154(b) by 0 days.

(21) Appl. No.: 13/699,934

(22) PCT Filed: Mar. 23, 2011

(86) PCT No.: PCT/NL2011/050200
§ 371 (c)(1),
(2), (4) Date: Feb. 11, 2013

(87) PCT Pub. No.: WO2011/149339
PCT Pub. Date: Dec. 1, 2011

(65) Prior Publication Data
US 2013/0137863 A1    May 30, 2013

(30) Foreign Application Priority Data
May 26, 2010    (EP) ..................... 10163881

(51) Int. Cl.
C07C 29/132    (2006.01)
C07D 201/08    (2006.01)
C07D 313/04    (2006.01)

(52) U.S. Cl.
CPC ............ *C07D 313/04* (2013.01); *C07C 29/132* (2013.01); *C07D 201/08* (2013.01)

(58) Field of Classification Search
CPC ... C07C 29/132; C07D 201/08; C07D 313/04
See application file for complete search history.

(56) References Cited

U.S. PATENT DOCUMENTS

| | | | |
|---|---|---|---|
| 3,000,880 A | | 9/1961 | Phillips et al. |
| 3,025,306 A | | 3/1962 | Guest et al. |
| 3,064,008 A | | 11/1962 | Phillips et al. |
| 3,070,633 A | * | 12/1962 | Torleif Utne et al. .......... 568/865 |
| 3,083,236 A | * | 3/1963 | Torleif Utne et al. .......... 568/865 |
| 3,317,563 A | | 5/1967 | Horlenko et al. |
| 4,324,710 A | | 4/1982 | Davis et al. |
| 4,400,468 A | * | 8/1983 | Faber ............................ 435/142 |

FOREIGN PATENT DOCUMENTS

| | | |
|---|---|---|
| CN | 101528725 | 9/2009 |
| JP | 55-024107 | 2/1980 |
| JP | 59-025383 | 2/1984 |
| JP | 61-048509 | 8/1984 |
| JP | 2003-321427 | 11/2003 |
| JP | 2010-070528 | 4/2010 |
| JP | 2010-208968 A | 9/2010 |
| WO | WO 94/25493 | 11/1994 |
| WO | WO 96/29322 | 9/1996 |
| WO | WO-2005/068643 A2 | 7/2005 |
| WO | WO-2005/123669 A1 | 12/2005 |
| WO | WO 2008/046790 | 4/2008 |
| WO | WO 2008/086122 A2 | 7/2008 |
| WO | WO-2011/149339 A1 | 12/2011 |

OTHER PUBLICATIONS

Ishii et al. (J. Org. Chem. 1998, 53, 5549-5552).*
Jung et al. (Organometallics 2002, 21, 5674-5677).*
Chinese Application No. 201180036114.6 Office Action dated Apr. 22, 2014.
Inoue et al., "A Convenient One-step Preparation of Oxacyclanes by Dehydration of Diols over Alumina", *The Chemical Society of Japan*, 1980, pp. 3,031-3,032.
Oka, "Studies on Lactone Formation in Vapor Phase. II.", *Synthesis of ε-Caprolactone*, Jul. 1961, vol. 35, pp. 562-566.
Marton et al., "Organotins as Etherification Catalysts. III. Etherifications and Hydro-Hydroxy-Eliminations Promoted by Butyltin Trichloride", *Tetrahedron*, 1989, vol. 45, pp. 7,099-7,108.
Chen et al., "Chemoselective Hydrogenolysis of Tetrahydropyran-2-methanol to 1,6-Hexanediol over Rhenium-Modified Carbon-Supporteded Rhodium Catalysts", *ChemCatChem*, 2010, pp. 2,547-2,555.

(Continued)

*Primary Examiner* — Valerie Rodriguez-Garcia
(74) *Attorney, Agent, or Firm* — Leason Ellis LLP.

(57) ABSTRACT

The present invention relates to a method for preparing caprolactone, comprising converting 5-hydroxymethyl-2-furfuraldehyde by hydrogenation into at least one intermediate compound selected from the group of 2,5-tetrahydrofuran-dimethanol, 1,6-hexanediol and 1,2,6-hexanetriol, and preparing caprolactone from said intermediate compound.

Further, the invention relates to a method for preparing 1,2,6-hexanetriol comprising preparing 5-hydroxymethyl-2-furfaldehyde from a renewable source, converting 5-hydroxymethyl-2-furfaldehyde into 2,5-tetrahydrofuran-dimethanol and converting 2,5-tetrahydrofuran-dimethanol into 1,2,6-hexanetriol.

Further, the invention relates to a method for preparing 1,6-hexanediol from 1,2,6-hexanetriol, wherein 1,2,6-hexanetriol is subjected to a ring closure reaction, thereby forming (tetrahydro-2H-pyran-2-yl)methanol, and the (tetrahydro-2H-pyran-2-yl)methanol is hydrogenated, thereby forming 1,6-hexane diol.

14 Claims, No Drawings

(56) References Cited

OTHER PUBLICATIONS

Dumesic et al., "Production of dimethylfuran for liquid fuels from biomass-derived carbohydrates", *Nature*, 2007, pp. 982-985.

Ishida et al., "Highly Efficient Catalytic Activity of Lanthanide(III) Ions for Conversion of Saccharides to 5-Hydroxymethyl-2-furfural in Organic Solvents", *Chemistry Letters*, 2000, pp. 22-23.

Binder and Raines, "Simple chemical transformation of lignocellulosic biomass into furans for fuels and chemicals", *J Am Chem Soc.*, 2009, vol. 131, pp. 1,979-1,985.

Dumesic et al., "Liquid-Phase Catalytic Processing of Biomass-Derived Oxygenated Hydrocarbons to Fuels and Chemicals", *Angewandte Chemie International Edition*, 2007, vol. 46, pp. 7,164-7,183.

Kuster, "5-Hydroxymethylfurfural (HMF). A Review Focussing on its Manufacture", *Starch*, 1990, vol. 42, pp. 314-321.

Schiavo et al., "Catalytic hydrogenation of 5-(hydroxymethyl)furfural in aqueous medisum", *Bulletin de la Soc. Chimique de France*, 1991, pp. 704-711.

Fetizon et al., "Oxydations par le carbonate d'argent sur celite-XIII:Preparation de lactones", *Tetrahedron*, 1975, vol. 31(2), pp. 171-176.

Kageyama et al., "A Facile Oxidative Lactonization of 1, ω-Diols With Sodium Bromite", *Chemistry Letters*, 1983, (7), pp. 1,097-1,100.

Bamoharram et al., "N-oxidation of pyridine carboxylic acids using hydrogen peroxide catalyzed by a green heteropolyacid catalyst: Preyssler's anion", *Journal of Molecular Catalysis A: Chemical*, Jun. 2006, vol. 252, pp. 219-225.

Zassinovich et al., "Asymmetric hydrogen transfer reactions promoted by homogeneous transition metal catalysts", *Chemical Reviews*, 1992, vol. 92, pp. 1,052-1,069.

De Vries eds., *"The Handbook of Homogeneous Hydrogenation"*, 2007, vol. 1, pp. 585-630, Wiley-Vch, Weinheim.

Ahn et al., "Racemization catalysts for the dynamic kinetic resolution of alcohols and amines", *Coordination Chemistry Reviews*, 2008, vol. 252, pp. 647-658.

International Search Report mailed Apr. 21, 2011 for the corresponding PCT Application No. PCT/NL2011/050200.

Meadows, Donella H., et al., "The Limits to Growth" pp. 56-60.

http://en.wikipedia.org/wiki/Limits_to_Growth. Jun. 24, 2014.

http://en.wikipedia.org/wiki/Club_of_Rome. Jul. 2014.

Terrence J. Connolly, et al. Efficient Synthesis of 8-Oxa-3-azabicyclo[3.2.1] octane Hydrochloride, *Organic Process Research & Development*, 2010, vol. 14, pp. 459-465.

\* cited by examiner

PREPARATION OF CAPROLACTONE, CAPROLACTAM, 2,5-TETRAHYDROFURAN-DIMETHANOL, 1,6-HEXANEDIOL OR 1,2,6-HEXANETRIOL FROM 5-HYDROXYMETHYL-2-FURFURALDEHYDE

CROSS-REFERENCE TO RELATED PATENT APPLICATIONS

This application is a U.S. National Phase Application under 35 U.S.C. §371 of International Patent Application No. PCT/NL2011/050200, filed Mar. 23, 2011, and claims priority to European Application No. 10163881.5, filed May 26, 2010, all of which are incorporated by reference to their entireties herein. The International Application was published as International Publication No. WO 2011/149339 A1 under PCT Article 21(2).

The invention relates to a method for preparing epsilon-caprolactone (hereinafter referred to as: caprolactone). The invention further relates to a method for preparing epsilon-caprolactam (hereinafter referred to as: caprolactam) from caprolactone.

Caprolactone is amongst others a useful product to prepare caprolactam from. It is also used as a raw material for the preparation of polyesters and resins. Caprolactam is a much used monomer for the preparation of polyamide.

Industrially, caprolactone and caprolactam are generally obtained from starting compounds that are obtained from mineral oil, such as benzene or toluene. In view of a growing desire to prepare materials using more sustainable technology it would be desirable to provide a method wherein caprolactone or caprolactam is prepared from a compound that can be obtained from a biologically renewable source. Furthermore, it would be desirable to provide a method that has a smaller ecological footprint than conventional chemical processes making use of bulk chemicals from petrochemical origin, in particular a method that requires less energy and/or has a lower carbon dioxide emission than said conventional processes.

It has been proposed to prepare caprolactam from a biochemically obtained intermediate, making use of genetically modified micro-organisms that are capable of converting a biologically renewable starting material (such as a sugar) into the intermediate. E.g. WO 2005/068643 describes the preparation of 6-aminocaproic acid by a genetically modified micro-organism. The 6-aminocaproic acid can thereafter be converted into caprolactam. Unfortunately, the titres of the obtained 6-aminocaproic acid and/or caprolactam in the Examples are low: in the order of ppm's, indicating that the reaction proceeds relatively slow, which is undesirable when operating at an industrial scale.

WO2005/123669 relates to the production of caprolactam by heating a salt of L-lysine in a solvent comprising an alcohol. The lysine may be obtained from biomass. The current production process of lysine from biomass, produces lysine at a price which is higher than the market price of caprolactam. In addition, the process uses expensive sulfonated hydroxylamine. Thereby this process is not really interesting for industrial use, in practice. Moreover, the production of sulfonated hydroxylamine is thought to be relatively energy-intensive.

It would be desirable to provide a method for preparing caprolactone or caprolactam from a starting compound that can be obtained from a biologically renewable source which does not require the use of a micro-organism. In particular, known processes making use of a micro-organism have a low conversion rate. Further, the final concentration of the product of interest (caprolactam, caprolactone or a precursor for any of these) is generally low. Therefore, it is contemplated a process based on a microorganism is not likely to produce caprolactone and caprolactam at competitive prices (at least not in the near future), because of the generally slow fermentation process and the low product concentration obtained in such a process.

Also, the isolation of the product of interest from the culture medium comprising the micro-organism used for the preparation of the product is generally relatively complex. Further, upscaling to a high-capacity plant and/or reducing reaction times may be an issue. Furthermore, there may be legal issues or consumer acceptance issues with respect to making use of genetically modified organisms that could frustrate implementation of the microbiological product of an intermediate for caprolactone or caprolactam on an industrial scale. Finally, fermentative processes may produce considerable waste streams (cell mass, growth medium) which will evoke considerable effort with respect to its disposal in an acceptable manner.

It is an object of the present invention to provide a method for preparing caprolactone or for preparing caprolactam from caprolactone from a starting compound that can serve as an alternative to known methods. In particular it is an object to provide a method for preparing caprolactone or for preparing caprolactam wherein one or more of the above mentioned issues with prior art technology are overcome or at least alleviated.

One or more further objects that may be addressed by the present invention will be apparent from the description herein below.

The inventors have found that it is possible to prepare caprolactone, caprolactam, 2,5-tetrahydrofuran-dimethanol, 1,6-hexanediol or 1,2,6-hexanetriol from 5-hydroxymethyl-2-furfuraldehyde (HMF), which can be prepared from a renewable resource.

Accordingly, the present invention relates to a method for preparing caprolactone, comprising converting 5-hydroxymethyl-2-furfuraldehyde by hydrogenation into at least one intermediate compound selected from the group of 2,5-tetrahydrofuran-dimethanol, 1,6-hexanediol and 1,2,6-hexanetriol, and preparing caprolactone from said intermediate compound.

Further, the present invention relates to a method for preparing 1,6-hexanediol, comprising preparing 5-hydroxymethyl-2-furfuraldehydefrom a renewable source, converting 5-hydroxymethyl-2-furfuraldehyde into 2,5-tetrahydrofuran-dimethanol and converting 2,5-tetrahydrofuran-dimethanol into 1,6-hexanediol.

Further, the present invention relates to a for preparing 1,6-hexanediol, comprising preparing 5-hydroxymethyl-2-furfuraldehydefrom a renewable source, converting 5-hydroxymethyl-2-furfuraldehyde into 2,5-tetrahydrofuran-dimethanol and converting 2,5-tetrahydrofuran-dimethanol into 1,6-hexanediol.

Further, the invention relates to a method for preparing 1,6-hexanediol from 1,2,6-hexanetriol, wherein 1,2,6-hexanetriol is subjected to a ring closure reaction, thereby forming (tetrahydro-2H-pyran-2-yl)methanol also abbreviated as 2-THPM), and the (tetrahydro-2H-pyran-2-yl)methanol 1 is hydrogenated, thereby forming 1,6-hexane diol.

Further, the present invention relates to a method for preparing caprolactam comprising reacting caprolactone prepared in a method according to the invention.

The invention is in particular advantageous in that the methods of the invention can readily be carried out on a large scale, because the HMF can be prepared from an abundant renewable source, such as fructose, and because the methods can be carried out without using a micro-organism to prepare the HMF from the renewable source and without using a micro-organism to prepare caprolactone, caprolactam, 2,5-tetrahydrofuran-dimethanol, 1,6-hexanediol or 1,2,6-hexanetriol from HMF.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "compound", this means "at least one" of that moiety, e.g. "at least one compound", unless specified otherwise.

Percentages (%) are weight percentages based on total weight, unless specified otherwise.

The term 'renewable source' is used herein in particular for materials that can be naturally replenished from living organisms. Fossil materials that have been transformed by geological processes, such as coal, oil or the like, are not renewable sources. More in particular, renewable sources include biomass which may be obtained from living material (e.g. plant matter, or components isolated there from such as lignocellulose, cellulose, starch, or glucose). A preferred source of biomass is agricultural waste (agro waste), which is formed by parts of agricultural crops that are not used for animal or human consumption. Normally it would be composted, largely to $CO_2$.

The HMF may in principle be obtained in any way, in particular from any renewable source. Preferably, the HMF has been prepared from a carbohydrate. The carbohydrate may in particular be selected from the group of fructose, glucose, sucrose, starch, cellulose and lignocellulose, including mixtures of any two or more of these, e.g. a mixture comprising glucose and fructose.

HMF can be prepared from fructose by an acid-catalysed dehydration reaction. This may be accomplished in a manner known per se, for instance in aqueous/organic mixtures, catalysed by sulphuric acid as described by Dumesic and co-workers (*Nature* 2007, 447, 982-985) or in DMSO catalysed by $LaCl_3$ (Ishida and co-workers, *Chemistry Letters* 2000, 22-23). Another method is described in Joseph B. Binder, and Ronald T. Raines, *J. Am. Chem. Soc.*, 2009, 131 (5), 1979-1985. Further, several reviews exist that describe the various processes, such as: Dumesic and co-workers, *Angewandte Chemie International Edition*, 2007 46 7164-7183 and B. F. M. Kusters, *Starch*, 1990, 8, 314-321. The contents of these publications regarding the reaction conditions of preparing HMF are incorporated by reference.

If a carbohydrate polymer is used, this may first be depolymerised to provide monosaccharide units (e.g. glucose or fructose). This may be accomplished in a manner known per se.

If glucose is used to prepare HMF, the glucose may first be converted into fructose, e.g. in a manner known per se. For instance, in a suitable process a product comprising glucose, such as corn syrup or another starch product, is first liquefied using an alpha-amylase, then the liquified product is enzymatically converted into glucose using a glucoamylase, and thereafter the product treated with glucoamylase is treated with glucose isomerase to give a mixture of fructose and glucose. This mixture can be separated, e.g. by simulated moving bed (SMB) to give what is called High Fructose Cornstarch Syrup (HFCS90), in case the starting product is corn syrup. This typically contains about 90 wt. % of fructose, based on dry weight. Of course, other syrups providing fructose may be used. HFCS90 is a preferred raw material for the production of HMF.

The conversion of HMF into 1,6-hexanediol may be done in any way.

In an advantageous embodiment, HMF is hydrogenated, thereby forming 2,5-tetrahydrofuran-dimethanol (THFDM), and thereafter THFDM is hydrogenated, thereby forming 1,6-hexanediol.

The 1,6-hexanediol can thereafter be converted into caprolactone.

This dual hydrogenation pathway is advantageous for a number of reasons. First of all the hydrogenolysis of the ether linkage needs high temperatures and high pressures. Under these conditions, undesired decarbonylation of HMF can be quite rapid. Therefore, it is preferred to first hydrogenate the aldehyde function to an alcohol and concomitantly the two double bonds of the furan under mild conditions to the THF-dimethanol before embarking on the hydrogenolysis of the two ether bonds that take place at higher temperatures. An advantage is that the first hydrogenation step can be performed with (cheap) Raney nickel. Potential impurities that are present in the HMF can be absorbed on this cheap catalyst before the process stream reaches the second, generally more expensive catalyst, thereby prolonging life-time of the second catalyst.

The hydrogenation of HMF to THFDM may be accomplished in a manner known per se, for instance as described by Schiavo et al. in J. Bulletin de la Societé Chimique de France (1991), p 704-11.

The hydrogenation of HMF to THFDM is usually carried out in the presence of hydrogen gas and a hydrogenation catalyst. A suitable hydrogenation catalyst may in particular be selected from the group of nickel catalysts, such as Raney nickel, or nickel nanoparticles, either in solution or on a carrier material, palladium, (e.g. on active coal or on another carrier material or in the form of nanoparticles), ruthenium (on carbon, in the form of nanoparticles or on another carrier material), rhodium (on carbon, in the form of nanoparticles or on another carrier material), platinum (on carbon, in the form of nanoparticles or on another carrier material), iron (on carbon, in the form of nanoparticles or on an other carrier material), gold (on carbon, in the form of nanoparticles or on other carrier material) or copper chromite. Nickel catalysts are preferred. Especially preferred is the use of Raney nickel or the use of nickel nanoparticles. It is also possible to use mixtures of catalysts. The ratio (W/W) of catalyst to HMF preferably is in the range of 1:1 to 1:1000 more preferred ratios are in the range of 1:2 to 1:100

As used herein, the term 'nanoparticles' means particles of a solid or semi-solid material having a weight average diameter, as determinable by scanning electron microscopy (SEM) or transmission electron microscopy (TEM) in the range of 1-1000 nm, in particular in the range of 5-500 nm.

The hydrogenation may conveniently be carried out in a flow reactor, such as a continuous stirred tank reactor (CSTR) or a tube reactor. The hydrogenation is preferably carried out in a solvent. Protic solvents or water are preferred solvents. Ethanol and propanol are particularly preferred solvents.

The molar ratio hydrogen gas to HMF is in general at least stoichiometric. Preferably an excess hydrogen gas is used. In particular, the molar ratio may be in the range of 10 to 2000. The hydrogen pressure preferably is between 1 and 12 MPa (10 and 120 bar) a more preferred range is 5-10 MPa (50-100 bar).

The temperature during the hydrogenation of HMF is usually chosen in the range of 50-250° C., in particular in the range of 60-150° C.; preferred is a temperature in the range of 70-110° C.

The hydrogenation of THFDM to 1,6-hexanediol may be accomplished in a manner known per se, for instance as described in U.S. Pat. No. 3,070,633, of which the contents are incorporated herein by reference.

In particular, the hydrogenation of THFDM may be carried out with hydrogen gas in the presence of a hydrogenation catalyst. A suitable hydrogenation catalyst may in particular be selected from the group of copper based catalysts, more in particular copper catalysts in which at least one further metal-element is present. The metal-element needs not be in a metallic state. Examples of copper catalyst including at least one further metal element are copper chromite and copper zinc.

Other catalysts that can be used include on rhodium on a solid support, such as rhodium on silica. The rhodium catalyst may be doped with one or more other elements. A preferred dopant is rhenium.

The hydrogenation of THFDM may be carried out in a conventional hydrogenation reactor, in particular in a CSTR or a tube reactor.

The hydrogenation of THFDM may be carried out in an inert solvent (e.g. an inert alcohol, such as methanol, ethanol or 1-propanol, a cycloalkane, such as cyclohexane, or in dimethoxymethane) or in the absence of an inert solvent.

The molar ratio hydrogen gas to THFDM is in general at least stoichiometric. Preferably an excess hydrogen gas is used. In particular, the molar ratio may be in the range of 10 to 2000.

The temperature during the hydrogenation of THFDM is usually chosen in the range of 80-350° C., in particular in the range of 120-330° C. A preferred temperature used may depend on the type of catalyst used. A preferred range for use with copper chromite is from 250-320° C. A preferred range for use with a Rh/Re catalyst is 120-250° C.

The hydrogen pressure during the hydrogenation of THFDM is usually chosen in the range of 5-20 MPa (50-200 bar); a preferred hydrogen pressure is between 8-12 MPa (80-120 bar).

The substrate to catalyst ratio (w/w) is usually chosen between 1:1 and 500:1; a preferred range is from 4:1 to 50:1.

In a preferred method, the first and the second hydrogenation step are directly coupled in the sense that the hydrogenation of HMF and the hydrogenation of the product of the HMF hydrogenation reaction are carried out in the same reactor, or in the sense that the product of the HMF hydrogenation reaction is continuously fed from a first reactor into a second reactor or from a first reaction zone inside a reactor (wherein the first hydrogenation reaction is carried out) into a second reaction zone inside that reactor (wherein the second hydrogenation step is carried out). In particular, the product of the HMF hydrogenation reaction may be directly fed from the first reactor or first reaction zone into the second reactor or first reaction zone. As used herein, 'directly fed' in particular means fed without intermediate storage of the product, without intermediate chemical reaction steps, and without intermediate purification steps. The second hydrogenation preferably takes place at higher temperature than the first hydrogenation. Accordingly, if desired, the feed may be heated when being transferred from the first to the second hydrogenation step. The product then can be converted into caprolactone.

In an embodiment of the above second hydrogenation, THFDM is hydrogenated to 1,2,6-hexanetriol or 1,6-hexanediol, which then can be converted into caprolactone, if desired.

Various catalysts can be used for this hydrogenation such as those based on palladium, nickel, rhodium, ruthenium, molybdenum, copper and chromium or mixtures thereof. Rhodium is a preferred metal. These catalysts may be deposited on a carrier material, such as silica, alumina or titanium oxide. In particular good results have been achieved with silica and titanium oxide. More in particular, good results were observed with G-6 3 silica from Fuji. The catalysts may also be doped with other elements such as rhenium, molybdenum and tungsten. A preferred catalyst is a rhodium-rhenium catalyst, in particular a rhodium-rhenium catalyst on silica. Much preferred is a Rh/Re catalyst on G-6 3 silica from Fuji.

The molar ratio of hydrogenation catalyst (such as rhodium) to dopant (such as rhenium) may be chosen within wide ranges, in particular in the range of 100:1 to 1:100. Preferably said ratio is in the range of 10:1 to 1:10; even more preferred is a ratio between 1:2 and 2:1.

Preferred temperatures are between 80-160° C., more preferred between 100-140° C.

Pressures may in particular be between 4 and 14 MPa, (between 40 and 140 bar) preferably between 6 and 10 MPa (between 60 and 100 bar).

The hydrogenation is preferably carried out in a solvent. Protic solvents or water are preferred solvents. Ethanol and propanol are more preferred solvents.

The 1,2,6-hexanetriol may be further hydrogenated to 1,6-hexanediol using a catalyst based on palladium, nickel, rhodium, ruthenium, copper and chromium or mixtures thereof. These catalysts may be deposited on a carrier material, for example silica. They may also be doped with one or more other elements, such as rhenium. A preferred catalyst is based on copper chromite.

The hydrogenation of 1,2,6-hexanetriol may be carried out in a conventional hydrogenation reactor, in particular in a CSTR or a flow reactor.

The hydrogenation of 1,2,6-hexanetriol may be carried out in an inert solvent (e.g. an inert alcohol, such as methanol, ethanol or 1-propanol, a cycloalkane, such as cyclohexane, or in dimethoxymethane) or in the absence of a solvent.

The molar ratio hydrogen gas to 1,2,6-hexanetriol is in general at least stoichiometric. Preferably an excess hydrogen gas is used. In particular, the molar ratio may be in the range of 10 to 2000.

The temperature during the hydrogenation of 1,2,6-hexanetriol is usually chosen in the range of 150-350° C. The temperature used may depend on the type of catalyst used. A preferred range for use with copper chromite is from 250-320° C.

The hydrogen pressure during the hydrogenation of 1,2,6-hexanetriol is usually chosen in the range of 5-20 MPa (50-200 bar), preferably in the range of 8-12 MPa (80-120 bar).

The substrate to catalyst ratio (w/w) usually is chosen in the range of 1:1 to 500:1; a preferred range is from 4:1 to 50:1.

In yet a further embodiment, HMF is directly converted into 1,6-hexanediol or 1,2,6-hexanetriol.

For instance, HMF may be hydrogenated with hydrogen in the presence of copper chromite as a hydrogenation catalyst, thereby producing 1,6 hexanediol or 1,2,6-hexanetriol. Suitable reaction conditions may e.g. be based on U.S. Pat. No. 3,083,236 on which the contents are incorporated by reference, in particular Example IV(a).

To suppress decarbonylation which may happen during hydrogenation, any of the hydrogenations in accordance with the invention may be carried out in the presence of CO (or a precursor for CO). A precursor for CO is a compound that under the hydrogenation conditions reacts to form CO. Precursors can in particular be selected from formic acid and formic acid esters. The amount of CO (or precursor for CO) relatively to hydrogen may in particular be in the range of 0.01-1, preferably in the range of 0.01 and 0.1 (mole to mole).

As indicated above, the invention also relates to a method for preparing 1,6-hexanediol from 1,2,6-hexanetriol, wherein 1,2,6-hexanetriol is subjected to a ring closure reaction, thereby forming (tetrahydro-2H-pyran-2-yl)methanol, and the (tetrahydro-2H-pyran-2-yl)methanol is hydrogenated, thereby forming 1,6-hexane diol. An advantage of such method is its high selectivity. The 1,2,6-hexanetriol may in principle be obtained in any way. Advantageously, it is made from THFDM, as described elsewhere in the present disclosure. Thereby, this method of preparing 1,6-hexanediol makes it possible to prepare 1,6-hexanediol from THFDM with a high overall selectivity.

The ring-closure reaction is conveniently catalysed by an acidic catalyst. This may be a solid acid catalyst, such as an acidic zeolite or a silica alumina catalyst or sulphated zirconia or an acidic ion exchange material, in particular an acidic ion exchange resin.

A suitable zeolite may in particular be selected from the group of ZSM-5 zeolites (silica) and beta-zeolites.

The acidic ion exchange material may in particular be selected from the group of materials having sulfonate groups as functional groups. In particular good results have been achieved with Smopex101®, sulfonated styrene divinylbenzene copolymers, such as Amberlyst™, or a sulfonated fluoropolymer, such as Nafion (e.g. Nafion SAC-13). In a further embodiment, the acidic catalyst is a soluble acid, such as an aromatic or aliphatic carboxylic acid, such as acetic acid, trifluoroacetic acid or benzoic acid or an aliphatic or an aromatic sulfonic acid, such as methylsulfonic acid, or trifluoromethylsulfonic acid or para-toluenesulfonic acid or it may be an aliphatic or an aromatic phosphonic acid such as benzene phosphonic acid. It may also be a mineral acid, such as sulfuric acid or phosphoric acid. In practice strong acids such as triflurosulfonic acid are preferred.

The ring-closure reaction can be carried out without a solvent; however use of a solvent is preferred, as it leads to higher selectivities. In practice any solvent that is acid stable at the reaction temperature and in which the substrate is soluble may be used. Sulfolane is a preferred solvent.

The reaction is conveniently carried out at elevated temperatures, in particular at a temperature of at least 50° C. In one embodiment of the invention the reaction takes place using gaseous reagents and a solid acid catalyst, preferably at a temperature of 200° C. or more. In another embodiment, the reaction takes place in the liquid phase, preferably at a temperature between 50 and 200° C., more preferably at a temperature between 100 and 150° C.

The hydrogenation of (tetrahydro-2H-pyran-2-yl)methanol to form 1,6-hexanediol may in principle be based on the hydrogenation conditions for hydrogenating THFDM, as described elsewhere in the present disclosure. In particular, good selectivity has been achieved with a rhodium-rhenium on silica catalyst. The molar ratio rhodium to rhenium may in particular be in the range of 100:1 to 1:100; preferably between 10:1 and 1:10; more preferred is a ratio between 1:2 and 2:1.

In a particularly preferred method according to the invention 1,2,6-hexanetriol is formed by hydrogenating 5-tetrahydrofuran-dimethanol, which may have been obtained from a renewable source, converting 1,2,6-hexanetriol, thus obtained, into (tetra-hydro-2H-pyran-2yl) methanol (2-THPM), and converting 2-THPM, thus obtained into 1,6-hexanediol. This method offers in particular a good selectivity and yield towards 1,2,6-hexanetriol and 1,6-hexanediol (an overall selectivity of at least 95% at 57% THFDM conversion has been found feasible, or an overall selectivity of at least 86% at complete THFDM conversion).

If desired, the method may be carried out at an incomplete conversion of 1,2,6-hexanetriol to 1,6-hexanediol. Then, the 1,6-hexanediol can be recovered from the product obtained from the reaction, which product then comprises both 1,2,6-hexanetriol and 1,6-hexanediol, and the 1,2,6-hexanetriol is then recycled to the reaction, if desired. The recovery of, 1,6-hexanediol can be accomplished in a manner known per se.

The formation of 1,2,6-hexanetriol and the formation of 1,6-hexanediol is generally catalysed by a hydrogenation catalyst. The formation of 2-THPM is generally catalysed by a ring closure catalyst (usually an acidic catalyst). The reaction steps may be carried out as described elsewhere herein. A preferred hydrogenation catalyst is a rhodium-rhenium catalyst, in particular a rhodium-rhenium catalyst on silica. A preferred ring closure catalyst is an acidic ion exchange material, in particular an acidic ion exchange resin or other ion exchange material having sulfonate groups as functional groups. Particularly preferred is a sulfonated fluoropolymer, such as Nafion.

In particular, good results have been achieved with such a method, wherein the 1,2,6-hexanetriol, the (2-tetra-hydro-2H-pyran-2yl) methanol, and the 1,6-hexanediol are formed in a one-pot process. It is contemplated that in particular the combined presence of a hydrogenation catalyst and a dehydration catalyst is advantageous for obtaining 1,6-hexanediol in a good yield, in particular a yield of 86% or more.

It is also possible to immobilise the hydrogenation catalyst onto the surface of an acidic solid acid catalyst. A preferred catalyst is Rh/Re on Nafion SAC-13.

The 1,6-hexanediol thus obtained may thereafter be used for the preparation of caprolactone in accordance with the invention, or used for another purpose.

The preparation of caprolactone from 1,6-hexanediol may be accomplished in any way. The preparation of caprolactone from 1,6-hexanediol is a so-called lactonisation of a diol. Such processes have been known in the art for over 40 years. For this conversion it is possible to use at least one catalyst selected from the group of homogeneous metal catalysts and heterogeneous metal catalysts. Many heterogeneous catalysts are suitable for this process. Preferably, homogeneous cyclisation catalysts are suitable. Catalysts may be based on ruthenium, osmium, rhodium, iridium, palladium, platinum, copper, cobalt, vanadium nickel or iron. Preferably, homogeneous cyclisation catalysts include ruthenium complexes, iridium complexes, cobalt complexes and nickel complexes. These metals may be entered as catalysts in an oxidised form or in a reduced form. Usually the heterogeneous catalyst will be supported on a carrier material. Examples of suitable carrier materials include silica, alumina, active carbon, and barium sulphate. For instance, caprolactone may be prepared in a method comprising mixing (vaporised) 1,6-hexanediol) with hydrogen, contacting the mixture with a catalyst, such as copper oxide, and recovering the formed caprolactone. Such conversion may be based on a method described in U.S. Pat. No. 3,317,563 (published in 1967), of which the contents, in particular the conditions specified in claims 1-6 and in the examples, are incorporated by reference.

Further, caprolactone may be prepared from 1,6-hexanediol, using silver carbonate, e.g. on celite. Suitable conditions may be based on Tetrahedron (1975), 31(2), 171-6, of which the contents are incorporated by reference.

Further, caprolactone may be prepared by treating 1,6-hexanediol with oxygen or a gas comprising oxygen (e.g. in air) in the presence of a transition metal catalyst; suitable examples are gold, nickel, ruthenium, rhodium, iridium, platinum or a palladium catalyst. The catalysts may be in the form of a homogeneous catalyst, containing ligands or they may be a heterogeneous catalyst on a carrier, such as silica, alumina or carbon, or they may be in the from of nanoparticles. Suitable conditions may for instance be based on JP 55 024 107, JP 61 048 509 or JP 2010208968A, of which the contents are incorporated by reference.

Further, caprolactone may be prepared by oxidative lactonisation of 1,6-hexanediol with sodium bromite, e.g. based on a method described in Chemistry Letters (1983), (7), 1097-100 or in JP 59 025 383, of which the contents are incorporated by reference.

Further, caprolactone may be prepared from 1,6-hexanediol in the presence of Preyssler's anion as a catalyst using hydrogen peroxide as oxidant. Suitable conditions may be based on Bamoharram et al., Journal of Molecular Catalysis A: Chemical 252 (2006) 90-95 of which the contents are incorporated by reference.

In an advantageous embodiment, the conversion of 1,6-hexanediol into caprolactone is carried out in the presence of a homogenous transition metal catalyst that is active as a redox catalyst. In general, any catalyst that is active as transfer hydrogenation catalyst or as racemisation catalyst is suitable. Many review articles and book chapters have been written about these catalysts, such as G. Zassinovich, G, Mestroni, S. Gladiali, *Chemical Reviews*, 1992, 92, 1051-1069. D. Klomp, U. Hanefeld, J. A. Peters in *Handbook of Homogeneous Hydrogenation*, J. G. de Vries, C. J. Elsevier, eds., Wiley-VCH, Weinheim, 2007, Vol 1, p 585-630. Yangsoo Ahn, Soo-Byung Ko, Mahn-Joo Kim, Jaiwook Park, Coordination Chemistry Reviews 252 (2008) 647-658. These catalysts can be based on ruthenium, osmium, rhodium, iridium, palladium, platinum, copper, cobalt, vanadium nickel or iron, in particular on ruthenium, iridium, cobalt and nickel. In general, the homogeneous catalyst for converting the 1,6-hexanediol into caprolactone will be in the form of a complex. In particular they may comprise one or more ligands selected from the group of phosphorus based ligands, alkoxides, amines, arenes, CO, substituted cyclopentadienes, unsubstituted cyclopentadienes; cyclometallatable CN ligands (i.e. ligands that bind via an anionic carbon atom and a neutral or anionic nitrogen atom that are linked together), CP ligands (i.e. ligands that bind via an anionic carbon atom and a neutral or anionic phosphorus atom that are linked together), CNN ligands (i.e. ligands that bind via an anionic carbon atom and two nitrogen groups that are linked together), CPP ligands (i.e. ligands that bind via one anionic carbon atom and two phosphorus atoms selected from the group of neutral phosphorus atoms and anionic phosphorus atoms that are linked together) and other cyclometallatable ligands.

Phosphorus based ligands include monodentate phosphines, bidentate phosphines, phosphites, phosphonites, phosphinites and phosphoramidites.

Amines include amines having more than one amine per molecule, e.g. diamines. Examples of amines that can be used as ligands include pyridine, bipyridine and 1,10-phenanthroline.

Cyclometallatable CN ligands include benzylamine, N-methyl-benzylamine N,N-dimethyl-benzylamine.

CP ligands include tris-ortho-tolyl-phosphine. CNN ligands include 1,3-dimethylaminomethylbenzene.

CPP ligands include 1,3-bis-(diphenylphopshinomethyl) benzene.

A ligand can further be selected from solvent molecules having ligand properties, such as tetrahydrofuran (THF) or acetonitrile. The complex of ligand(s) and metal may also have one or more anions selected from the group of halides, carboxylates and non-coordinating anions, such as $BF_4^-$ or $PF_6^-$.

Good results have been achieved with iridium complexes, such as $[Cp*IrCl_2]_2$ or with ruthenium complexes, in particular with complexes of the type $Ru(phosphine)_nX_m$ where n=1, 2,3 or 4 and m=1, 2 or 3, or mixtures thereof. Also particularly suitable are complexes made in situ by the addition of monodentate or bidentate phosphorus ligands to $[Ru(arene)Cl_2]_2$ in which arene is benzene, cymene or trimethylbenzene.

The molar ratio of substrate to catalyst may in particular be between 1 and 1,000,000. Preferred is a molar ratio in the range of 100-200,000.

Often these catalysts need the presence of a catalytic amount of a base, for good catalytic activity. The base can be a mineral base, for instance a mineral base selected from the group of KOH, NaOH, $KHCO_3$, $K_2CO_3$, $Na_2CO_3$, $Cs_2CO_3$ and $NaHCO_3$, or it can be an organic base, for instance triethylamine, tributylamine or DABCO (1,4 diazabicyclo [2.2.2]octane).

The molar ratio of the catalyst to the base may vary considerably and may also be dependent on the catalyst employed. In general said molar ratio will be in the range of from 1:1 to 1:100,000; preferably from 1:5 to 1:100.

The lactonisation may be carried out as a dehydrogenation in which hydrogen is formed as side product. This hydrogen is optionally used for the hydrogenation of HMF to 1,6-hexanediol or of THFDM to 1,6-hexanediol or of 1,2,6-hexanetriol to 1,6-hexanediol. It is also possible to carry out the lactonisation in the presence of a hydrogen acceptor or an oxidant. Suitable hydrogen acceptors include ketones, such as acetone, or methyl isobutylketone (MIBK) or alkenes such as isobutene. The resulting alcohols may be used as such or may be dehydrogenated to regenerate the ketone and an equivalent of hydrogen. The lactonisation may also be carried out in the presence of an oxidant such as oxygen or hydrogen peroxide.

The lactonisation may be carried out without a solvent or in the presence of a suitable solvent that is inert to the reaction conditions, such as a hydrocarbon or a halogenated hydrocarbon. It is also possible to use a ketone which participates in the reaction as a hydrogen acceptor as solvent. In a preferred method wherein use is made of a homogenous cyclisation catalyst, the conversion of the 1,6-hexanediol into caprolactone is carried out in the presence of a phase transfer catalyst. The phase transfer catalyst (PTC) is preferably selected from the group of quaternary ammonium salts, in particular from the group of tetraalkylammonium salts, and polyalkylene glycols, in particular polyethylene glycols. The alkyl group will generally comprise 1 to 20 carbon atoms. The counter ion may be a halide, such as chloride or bromide, or $HSO_4^-$ or acetate or tosylate. In general the choice of the anion is not critical. Examples of suitable PTC's are tetrabutylammonium bromide or benzyltrimethylammonium chloride or tetra-octylammonium hydrogen sulfate. The amount of PTC with respect to the amount of substrate is between 0.01-50 mol %; more preferred is between 1-25 mol %. The temperature of the reaction may vary between 50-200° C.; more preferred between 80-150° C.

Caprolactam can be prepared from caprolactone in a manner known per se. In a preferred method of the invention caprolactam is prepared in a method comprising reacting caprolactone with ammonia. Suitable processes are e.g. described in U.S. Pat. No. 3,000,880, U.S. Pat. No. 3,025,306 and U.S. Pat. No. 3,064,008, of which the contents are incorporated by reference, in particular the contents dealing with the reaction conditions for preparing caprolactam from caprolactone.

The invention will now be illustrated by the following examples.

EXAMPLE 1

Direct Hydrogenation of HMF to 1,6-hexanediol

In a stirred autoclave of 100 ml 0.1 g of copper chromite and 0.06 g of Pd on carbon (10%) was added to a solution of 0.5 g of HMF in 25 ml of methanol. The lid of the autoclave was closed, stirring was started at 1000 rpm and after three vacuum/nitrogen cycles the autoclave was pressurised at 3 MPa 112 and the temperature was raised to 80° C. After 1.5 h the hydrogen pressure was raised to 15 MPa and the temperature to 270° C. The autoclave was kept stirred under these conditions for a further 14.5 h. After cooling to ambient temperature the pressure was released and the contents of the autoclave were subjected to GC analysis, which showed the presence of 4.2% of 1,6-hexanediol and 2.3% of 1,2,6-hexanetriol.

EXAMPLES 2-15

Hydrogenation of HMF to THFDM

In a stirred autoclave of 100 ml 0.05 g of 5 Mol % Ru/C (Aldrich) was added to a solution of 0.5 g of HMF in 30 ml of methanol. The lid of the autoclave was closed, stirring was started at 1000 rpm and after three vacuum/nitrogen cycles the autoclave was pressurised at 5 MPa $H_2$ and the temperature was raised to 75° C. After 1.5 h the hydrogen pressure was raised to 9 MPa and the temperature to 200° C. The autoclave was kept stirred under these conditions for a further 14 h. After cooling to ambient temperature the pressure was released and the contents of the autoclave were subjected to GC analysis, which showed the presence of 30% of THFDM.

In the same manner several other catalysts were tested in this hydrogenation and the results are collected in Table 1

TABLE 1

Hydrogenation of HMF to 2,5-THF-dimethanol [a]

| Example | Catalyst | %-2,5-THF-dimethanol |
|---|---|---|
| 2 | Ru/C (ALD) 5% | 30 |
| 3 | Ru/C (JM) 5% | 46 |
| 4 | Ru/C (JM) 0.5% | 12 |
| 5 | Pd/C 10% | 38 |
| 6 | G-69B (Sud) | 55 |
| 7 | Ra—Ni | 79 |
| 8 | CuCr (ALD) | 9 |
| 9 | CuCr (AC) | 11 |
| 10 | CuCr—Pd/C | 62 |

Suppliers between brackets: ALD = Aldrich; JM = Johnson Matthey; Sud = sudchemie; AC = Across
[a] In all cases 100% conversion of the starting material was observed.

From these results it is clear that Raney nickel (Ra—Ni) is a very good catalyst for this conversion.

EXAMPLES 11-15 (Summarised in Table 2)

Show the Effect of the Temperature on the hydrogenation of HMF with Raney Nickel at 9 MPa in Methanol.

TABLE 2

Hydrogenation of HMF with Ra—Ni at different temperatures.[a]

| Examples | Temperature | Yield of 2,5-THF-dimethanol |
|---|---|---|
| 11 | 250 | 50 |
| 12 | 200 | 79 |
| 13 | 150 | 88 |
| 14 | 100 | 99 |
| 15 | 75 | 91 |

[a] In all cases 100% conversion of the starting material was observed.

From these examples it is clear that 100° C. is an optimal temperature for the hydrogenation of HMF to THFDM with Ra—Ni, and that Ra—Ni is a suitable catalyst.

EXAMPLE 16-22

Hydrogenation of THFDM to 1,6-hexanediol

In a stirred autoclave of 100 ml 0.1 g of copper chromite was added to a solution of 0.5 g of THFDM in 30 ml of n-propanol. The lid of the autoclave was closed, stirring was started at 1000 rpm and after three vacuum/nitrogen cycles the autoclave was pressurised at 10 MPa $H_2$ and the temperature was raised to 260° C. The autoclave was kept stirred under these conditions for a further 6 h. After cooling to ambient temperature the pressure was released and the contents of the autoclave were subjected to GC analysis, which shows the presence of 17.3% of 1,6-hexanediol and 3.7% of 1,2,6-hexanetriol. Other catalysts were tested under similar conditions (Table 3).

TABLE 3

Hydrogenation of THFDM

| Example | Catalyst | Conversion | Yield 1,6-hexanediol | Yield 1,2,6-hexanetriol |
|---|---|---|---|---|
| 16 | CuCr | 70% | 17.3% | 3.7% |
| 17 | CuZn (JM PR-A) | 26% | 1.8% | 5.4% |
| 18 | CuZn (JM PR-B) | 71% | 2.1% | 2.0% |
| 19 | CuZn (Sud T-2 130) | 28% | 2.2% | 1.1% |

In the Examples 20-22 the effect of temperature and duration on the hydrogenation of THFDM with CuCr was investigated in experiments which were performed otherwise identical to Example 16.

TABLE 4

Hydrogenation of THFDM with CuCr

| Example | Time | Temperature | 1,6-hexanediol | 1,2,6-hexanetriol |
|---|---|---|---|---|
| 20 | 6 h | 260° C. | 17% | 4% |
| 21 | 15 h | 260° C. | 22% | 1% |
| 22 | 6 h | 320° C. | 15% | 0% |

Preparation of Rh/Re Catalyst for use in Examples 23-32

Silica was precalcined at 773K for 3 h prior to impregnation unless otherwise mentioned. Two grams of silica were stirred with an aqueous solution of 176 mg of $RhCl_3$ during 2 hours. Thereafter the water was filtered off and the remaining solid dried at 383K for 13-14 h. Next, the solid was impregnated with an aqueous solution of 113 mg of $NH_4ReO_4$, after filtration and drying as before the final step was calcination in air at 773K for 3 h.

The catalyst was measured to have a Rh-content of 4 wt-% and a Re-content of 2 wt %.

It is also possible to apply the two solutions in a single impregnation step. The catalyst prepared in this fashion was tested in Example 24.

It is also possible to use carrier materials other than silica such as Alumina or Cerium oxide.

For comparison purposes catalysts were also prepared that were only impregnated with Rh (tested in Example 25) or with Re (tested in Example 26) according to the procedure described above. Results with all four types of catalysts can be found in Table 5.

EXAMPLES 23-33

Preparation of 1,2,6-hexanetriol

In an autoclave of 60 ml, 25 mg of the Rh/Re catalyst prepared according to the procedure above was added to a solution of 100 mg of THFDM in 29 ml of water. The autoclave was closed, stirring was started at 1000 rpm and after 3 vacuum nitrogen cycles the hydrogen pressure was set at 1 MPa and the temperature at 120° C. After 1 h the hydrogen pressure was raised to 8 MPa. After 4 h the autoclave was allowed to cool to ambient temperature and the pressure was released. Analysis of the contents by GC showed a conversion of THFDM of 16.5%, a yield of 1,2,6-hexanetriol of 7.5% and a yield of 1,2,6-hexanetriol of 0.4%.

In the examples 23-33 different catalysts, catalyst mixtures and carrier materials were tested in the hydrogenation of THFDM. These reactions were performed in capped glass vials that contained a stir bar the septum of which had been pierced with a needle to equalize the pressure. Up to 6 of these vials were hydrogenated at the same time in the autoclave.

These experiments show it is possible to hydrogenate THFDM with high selectivity to 1,2,6-hexanetriol, when a combination of rhodium and rhenium is used.

EXAMPLE 34

Hydrogenation of 1,2,6-hexanetriol to 1,6-hexanediol

In an autoclave of 100 ml 0.1 g of CuCr(BASF) was added to a solution of 0.5 g of 1,2,6-hexanetriol in n-propanol. After three vacuum/nitrogen cycles stirring was started at 1000 rpm, the autoclave was pressurised with hydrogen to 10 MPa and the temperature is raised to 260° C. After 6 h the autoclave was allowed to come to ambient temperature and the pressure was released. GC of the contents showed a 40% yield of 1,6-hexanediol.

EXAMPLE 35

Lactonisation of 1,6-hexanediol

A 50 ml three-necked flask flask was provided with a reflux condensor a nitrogen inlet and a magnetic stir bar. $K_2CO_3$ (0.2 mmol) was added, followed by 1 mmol of 1,6-hexanediol and 25 ml of acetone. The solution was subjected to 3 vacuum/nitrogen cycles and 2 mol % of $[Ir(Cp*)Cl]_2$ (Cp*=pentamethyl-cyclopentadiene) was added. The mixture was kept under nitrogen and heated under reflux while stirring for 24 h. After this period GC showed 44% conversion with a selectivity of 33% to caprolactone.

EXAMPLE 36-3

Lactonisation of 1,6-hexanediol

In examples 36-38 other catalysts were tested in the lactonisation of 1,6-hexanediol to caprolactone (Table 6).

TABLE 5

Hydrogenation of THFDM to mainly 1,2,6-hexanetriol

| Example | Catalyst | %-conv | %-yield 1,6 | %-yield 1,2,6 | %-sel 1,6 | %-sel 1,2,6 |
|---|---|---|---|---|---|---|
| 23 | Rh—Re/SiO$_2$$^a$ (2-step)$^d$ | 16.5 | 0.4 | 7.5 | 2.2 | 45.7 |
| 24 | Rh—Re/SiO$_2$$^a$ (1-step)$^e$ | 15.3 | 0.0 | 6.8 | 0.0 | 44.2 |
| 25 | Rh/SiO$_2$ | 3.1 | 0.0 | 0.0 | 0.0 | 0.0 |
| 26 | Re/SiO$_2$ | 3.4 | 0.0 | 0.0 | 0.0 | 0.0 |
| 27 | Rh—Re/CeO$_2$ (2-step)$^d$ | 9.5 | 0.0 | 2.0 | 0.0 | 21.0 |
| 28 | Rh—Re/Al$_2$O$_3$ (2-step)$^d$ | 4.0 | 0.0 | 0.0 | 0.0 | 0.0 |
| 29 | Rh/Al$_2$O$_3$ + Re | 10.5 | 0.0 | 4.4 | 0.0 | 42.4 |
| 30 | Rh/Al$_2$O$_3$ | 2.1 | 0.0 | 0.0 | 0.0 | 0.0 |
| 31 | Rh—Re/SiO$_2$$^b$ (2-step)$^d$ | 14.1 | 0.0 | 10.4 | 0.0 | 73.9 |
| 32 | Rh—Re/SiO$_2$$^c$ (2-step)$^d$ | 30.9 | 1.0 | 25.8 | 3.4 | 83.5 |
| 33 | Rh 4 wt. % Re/Rh 0.5 (mol/mol) | 11 | 0.0 | 10.3 | 0.0 | 94 |

$^a$Silica grade 9385 (Aldrich);
$^b$Silica G-6 5 mikron (Fuji Silysia);
$^c$Silica G-6 3 mikron (Fuji Silysia);
$^d$First impregnation with Rh, followed by impregnation with Re in a second step.
$^e$Simultaneous impregnation with Rh and Re in a single step

TABLE 6

Lactonisation of 1,6-hexanediol

| Example | Catalyst | Conversion | Selectivity to caprolactone |
|---|---|---|---|
| 35 | [Cp*IrCl$_2$]$_2$ | 44% | 33% |
| 36 | RuCl$_2$(PPh$_3$)$_3$ | 31% | 81% |
| 37 | [p-cymenRuCl$_2$]$_2$ + dppp* | 54% | 87% |
| 38 | RuCl$_3$ + dppp | 3% | 90% |

*dppp = 1,3-(Diphenylphosphino)propane

In Examples 39-45 three catalysts were tested in the same way as in Example 35, with the difference that different solvents were tested.

TABLE 7

Lactonisation of 1,6-hexanediol

| Example | Catalyst | Solvent | Conversion | Selectivity to caprolactone |
|---|---|---|---|---|
| 39 | [Cp*IrCl$_2$]$_2$ | acetone | 44% | 33% |
| 40 | | MIBK | 10% | 57% |
| 41 | RuCl$_2$(PPh$_3$)$_3$ | acetone | 31% | 81% |
| 42 | | MIBK | 64% | 76% |
| 43 | | CHCl$_3$ | 3% | |
| 44 | [p cymeneRuCl$_2$]$_2$ + dppp | acetone | 54% | 87% |
| 45 | | MIBK | 87% | 90% |

EXAMPLES 46 and 47

Lactonisation of 1,6-hexanediol

In these examples the lactonisation of 1,6-hexanediol was performed according to the method described in example 34 using MIBK as solvent and K$_2$CO$_3$ as base. In these two experiments 20 mol % of Bu$_4$NBr was additionally added. These results show that the addition of a phase transfer catalyst to these lactonisation reactions is beneficial. The results are displayed in Table 8.

TABLE 8

| Example | Catalyst | PTC | Conversion | Selectivity to caprolactone |
|---|---|---|---|---|
| 46 | RuCl$_2$(PPh$_3$)$_3$ | Bu$_4$NBr (20 mol %) | 95% | 97% |
| 47 | [RuCl$_2$(p-cymene)]$_2$, dppp | Bu$_4$NBr (20 mol %) | 99% | 98% |

EXAMPLES 48-49

Preparation of 1,6-hexanediol from 1,2,6-hexanetriol
1,2,6-hexanetriol was converted into (tetrahydro-2H-pyran-2-yl)methanol

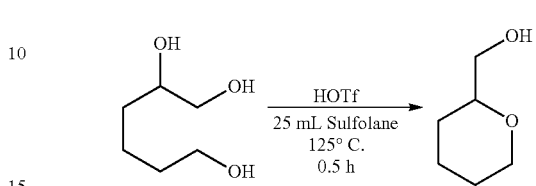

The reaction was performed in a 100 mL three-neck round bottom flask. 1,2,6-hexanetriol (3.3543 g, 25.0 mmol) was dissolved in sulfolane (25 mL). Then, trifluoromethane-sulfonic acid (13.3 µL, 0.15 mmol) were added. The reaction mixture was heated to 125° C. for 30 mins. GC shows full conversion with 100% selectivity to the desired product.

Next, 0.1 g of (tetrahydro-2H-pyran-2-yl)methanol (THPM) was put in an 8 ml vial and the vial was filled with water (2 g) as the solvent. The catalyst (10 mg, 10%-wt to THPM) was added to the solution. The vial was then put in a stainless steel autoclave. The autoclave was sealed and five times pressurised with hydrogen gas and vented in order to remove air. First, the pressure and temperature were set to 1 MPa and 180° C., respectively. After 1 h, the pressure was increased to 8 MPa and the reaction was stopped after 3.5 h.

The results are shown in Table 9.

TABLE 9

| Example | Catalysts | %-conv | %-sel. to 1,6-hexanediol |
|---|---|---|---|
| 48 | Rh—Re/SiO$_2$ JM [a] | 16.6 | 100 |
| 49 | Rh—Re/SiO$_2$ Fuji [b, c] | 8.3 | 100 |

[a] 6.5%-wt Rh
[b] 4%-wt Rh
[c] when the reaction was performed for 20 h (instead of 3.5 h): 8.6%-conv and 100%-selectivity to 1,6-hexanediol

EXAMPLE 50-62

Preparation of 1,6 hexanediol from THFDM (via 1,2,6-HT and 2-THPM)

1,6 hexanediol was prepared from THFDM using the following reactions in a single pot.

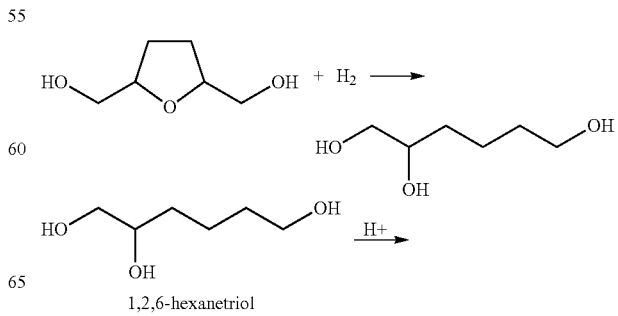

1,2,6-hexanetriol

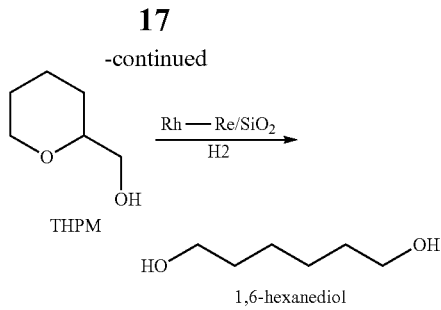

The reactions were carried out on 100 mg of 2,5-THF-dimethanol in 2 g of water in a single stirred autoclave (one-pot process), with Rh—Re (6.5 wt. % Rh; Re/Rh=0.5) on SiO$_2$ from Johnson Matthey as hydrogenation catalyst (25 weight % w.r.t. the starting material) and various acidic catalysts (ring closure catalyst) in 15 weight % w.r.t. the starting material. The conditions were as follows: temperature=120° C. The pressure was 1 MPa for the first hour and thereafter 8 MPa for the remaining 19 hours.

The results are shown in Table 10. The selectivity to the major side product, 1,5 hexanediol, is also shown.

TABLE 10

| Example | acidic catalyst | t$_2$ (h) | %-conv | %-sel to 1,6 hexanediol | %-sel to 1,5 hexanediol | %-sel to 1,2,6 hexanetriol |
|---|---|---|---|---|---|---|
| 50 | Sulfonated carbon | 20 | 65 | 26 | 4 | 70 |
| 51 | Sulfonated carbon | 4 | 22 | 9 | 1 | 90 |
| 52 | Zeolite 1 | 20 | 82 | 39 | 9 | 52 |
| 53 | Zeolite 1 | 4 | 37 | 15 | 0 | 81 |
| 54 | Zeolite 2 | 20 | 92 | 61 | 12 | 27 |
| 55 | Zeolite 2 | 4 | 38 | 18 | 0 | 77 |
| 56 | Zeolite 3 | 20 | 87 | 47 | 7 | 46 |
| 57 | Zeolite 3 | 4 | 29 | 9 | 0 | 88 |
| 58 | Nafion ® SAC-13 | 20 | 100 | 86 | 14 | 0 |
| 59 | Nafion ® SAC-13 | 4 | 57 | 21 | 0 | 74 |
| 60 | Sulph-ZrO$_2$ | 20 | 88 | 49 | 9 | 42 |
| 61 | Amberlyst ™-16 | 20 | 91 | 56 | 10 | 34 |
| 62 | Smopex ®-101 | 20 | 93 | 60 | 10 | 30 |

Zeolite 1 is ZAP-27 (Si/Al = 12.5) and Zeolite 2 is ZAP-55 (Si/Al = 21.1) (these are types of ZSM-5 silica see: I. Meli án-Cabrera, C. Mentruit, J. A. Z. Pieterse, R. W. van den Brink, G. Mul, F. Kapteijn, .A. Moulijn, Catalysis Communications 6 (2005) 301-305.); and Zeolite 3 is 814E (a type of beta zeolite from Zeolyst International, SiO$_2$/Al$_2$O$_3$ Molar Ratio: 25). For the preparation of sulfonated carbon, see Example XX below It is shown that 100% conversion is obtained with sulfonated fluoropolymer (Nafion® SAC-13) as the acidic catalyst, within 20 hours, with 86% selectivity towards 1,6 hexanediol. The results for other catalysts are also satisfactory in that the selectivity to desired products (1,6-hexanediol and 1,2,6 hexanetriol) is high (more than 85%)

EXAMPLE 63

Preparation of Sulfonated Carbon 20 g of D-glucose was heated up to 400° C. (5° C./min) under a N$_2$ flow in a tubular oven for 15 h to produce brown-black solids. The obtained solids were weighed and then ground to powder. The produced powder was heated in concentrated H$_2$SO$_4$ (95-97% Merck) at 150° C. under N$_2$ for 15 h to introduce SO$_3$H groups into the aromatic carbon rings (30 ml H$_2$SO$_4$ per gram). After cooling to room temperature, the solids were filtered using 1000 cm$^3$ of distilled water. Subsequently, the black precipitates were washed repeatedly with hot distilled water (T>80° C.) until no acidity was detected in the residual water. The material was placed in a petri dish and dried overnight in an oven at 90° C. Composition: CH0.57O$_{0.57}$S$_{0.013}$. Total acidity: 1,61 mmol/g. SO$_3$H-density: 0.61 mmol/g

The invention claimed is:

1. A method for preparing caprolactone, comprising the steps of:
   (a) hydrogenating 5-hydroxymethyl-2-furfuraldehyde to 2,5-tetrahydrofuran-dimethanol,
   (b) converting 2,5-tetrahydrofuran-dimethanol by hydrogenation, whereby at least part of the 2,5-tetrahydrofuran-dimethanol that is hydrogenated forms 1,2,6-hexanetriol in the presence of a rhodium-rhenium catalyst,
   (c) converting 1,2,6-hexanetriol to 1,6-hexanediol by hydrogenation, and
   (d) converting 1,6-hexanediol into caprolactone.

2. The method according to claim 1, wherein the 5-hydroxymethyl-2-furfuraldehyde is obtained from a renewable source.

3. The method according to claim 1, wherein 5-hydroxymethyl-2-furfuraldehyde is hydrogenated in the presence of a Raney nickel hydrogenation catalyst or another nickel catalyst.

4. The method according to claim 1, wherein 2,5-tetrahydrofuran-dimethanol is converted into 1,2,6-hexanetriol further in the presence of a copper chromite hydrogenation catalyst.

5. The method according to claim 1, further comprising the steps of:
   converting 1,2,6-hexanetriol into (2-tetra-hydro-2H-pyran-2yl) methanol by a ring closure reaction; and
   converting (2-tetra-hydro-2H-pyran-2yl) methanol into 1,6-hexanediol by hydrogenation.

6. The method according to claim 5, wherein the steps of producing the 1,2,6-hexanetriol, the (2-tetra-hydro-2H-pyran-2yl) methanol, and the 1,6-hexanediol are performed in a one-pot process.

7. The method according to claim 1, wherein the conversion of 1,6-hexanediol into caprolactone is carried out in the presence of a homogenous cyclisation catalyst, a base and a phase transfer catalyst.

8. The method according to claim 7, wherein
   the cyclisation catalyst is selected from the group consisting of ruthenium complexes, iridium complexes, cobalt complexes and nickel complexes,
   the base is selected from the group consisting of alkali metal carbonates, and
   the phase transfer catalyst is selected from the group consisting of quaternary ammonium salts and polyalkylene glycols.

9. The method according to claim 1, wherein 5-hydroxymethyl-2-furfuraldehyde is prepared from a carbohydrate.

10. The method according to claim 9, wherein the carbohydrate is selected from the group consisting of fructose, glucose, starch, cellulose and lignocellulose, including mixtures thereof.

11. The method according to claim 1, wherein an overall selectivity towards 1,6-hexanediol and 1,2,6-hexanetriol is at least 86% when 2,5-tetrahydrofuran-dimethanol conversion is complete.

12. The method according to claim 1, wherein a yield of 1,6-hexanediol from conversion of 2,5-tetrahydrofuran-dimethanol is at least 86%.

13. The method according to claim 1, wherein an overall selectivity towards 1,2,6-hexanetriol and 1,6-hexanediol is at least 95% at 57% THFDM conversion.

14. The method according to claim 1, wherein part of the 2,5-tetrahydrofuran-dimethanol that is hydrogenated forms 1,6-hexanediol.

* * * * *